United States Patent
Zollinger et al.

(10) Patent No.: US 10,112,921 B2
(45) Date of Patent: Oct. 30, 2018

(54) METHOD FOR PREPARATION OF THIOPHENE-2-CARBONYL CHLORIDES WITH OXALYL CHLORIDE

(71) Applicant: LONZA LTD, Visp (CH)

(72) Inventors: Daniel Zollinger, Sierre (CH); Florencio Zaragoza Doerwald, Visp (CH)

(73) Assignee: LONZA LTD, Visp (CH)

( * ) Notice: Subject to any disclaimer, the term of this patent is extended or adjusted under 35 U.S.C. 154(b) by 0 days.

(21) Appl. No.: 15/751,957

(22) PCT Filed: Nov. 2, 2016

(86) PCT No.: PCT/EP2016/076317
§ 371 (c)(1),
(2) Date: Feb. 12, 2018

(87) PCT Pub. No.: WO2017/076844
PCT Pub. Date: May 11, 2017

(65) Prior Publication Data
US 2018/0230121 A1    Aug. 16, 2018

Related U.S. Application Data

(60) Provisional application No. 62/250,587, filed on Nov. 4, 2015.

(30) Foreign Application Priority Data

| Nov. 4, 2015 | (EP) | 15192880 |
| Jan. 6, 2016 | (EP) | 16150309 |
| Jan. 8, 2016 | (EP) | 16150583 |
| Jan. 8, 2016 | (EP) | 16150642 |
| Jan. 12, 2016 | (EP) | 16150854 |
| Jan. 19, 2016 | (EP) | 16151908 |
| Feb. 22, 2016 | (EP) | 16156620 |
| Aug. 2, 2016 | (EP) | 16182376 |

(51) Int. Cl.
*C07D 333/38*   (2006.01)
*C07D 413/14*   (2006.01)
*C07D 413/04*   (2006.01)

(52) U.S. Cl.
CPC ......... *C07D 333/38* (2013.01); *C07D 413/04* (2013.01); *C07D 413/14* (2013.01)

(58) Field of Classification Search
CPC .... C07D 413/14; C07D 413/04; C07C 333/38
USPC ........................................................ 544/137
See application file for complete search history.

(56) References Cited

U.S. PATENT DOCUMENTS

| 4,321,399 A | 3/1982 | Jones et al. |
| 6,107,519 A | 8/2000 | Pearlman |
| 2003/0153610 A1 | 8/2003 | Straub et al. |
| 2015/0133657 A1 | 5/2015 | Singh et al. |

FOREIGN PATENT DOCUMENTS

WO    2014/008257 A2    1/2014

OTHER PUBLICATIONS

International Search Report and Written Opinion dated Dec. 6, 2016 from International Application No. PCT/EP2016/076317, 14 Pages.
Kuehnhanss et al., "Contribution on the Carboxylation of Thiophene by Means of Urea Chloride and Oxalyl Chloride", Journal Fuer Praktische Chemie, 1956, vol. 3, No. 3-4, pp. 137-145 and English translation.
Roehrig et al., "Discovery of the Novel Antithrombotic Agent 5-Chloro-N-({(5S)-2-oxo-3-[4-(3-oxomorpholin-4-yl) phenyl]-1,3-oxazolidin-5-yl}methyl)thiophene-2-carboxamide (BAY 59/7939): An Oral, Direct Factor Xa Inhibitor", Journal of Medicinal Chemistry, 2005, vol. 48, pp. 5900-5908.
Edwards et al., "Friedel-Crafts Acylation of Thiophene with Mixed Acetic Anhydrides", J. Org. Cherm., 1966, vol. 31, pp. 1283-1285.
Geobaldo et al., "Spectroscopic study in the UV-Vis, near and mid IR of cationic species formed by interaction of thiohene, dithiohene and terthiophene with the zeolite H-Y", Phys. Chem. Chem. Phys., 1999, vol. 1, pp. 561-569.
International Preliminary Report on Patentability dated Nov. 10, 2017 from International Application No. PCT/EP2016/076317, 7 Pages.
Written Opinion of the International Preliminary Examining Authority dated Sep. 26, 2017 from International Application No. PCT/EP2016/076317, 7 Pages.

*Primary Examiner* — Kahsay Habte
(74) *Attorney, Agent, or Firm* — MH2 Technology Law Group, LLP

(57) ABSTRACT

The invention discloses a method for the preparation of thiophene-2-carbonyl chlorides starting from thiophenes with oxalyl chloride at elevated temperature with short reaction time.

14 Claims, No Drawings

METHOD FOR PREPARATION OF THIOPHENE-2-CARBONYL CHLORIDES WITH OXALYL CHLORIDE

CROSS-REFERENCE TO RELATED APPLICATIONS

This application is a U.S. National Stage application of PCT/EP2016/076317 filed 2 Nov. 2016, which claims priority to U.S. Provisional Patent Application No. 62/250,587 filed 4 Nov. 2015, European Patent Application No. 15192880.1 filed 4 Nov. 2015, European Patent Application No. 16150309.9 filed 6 Jan. 2016, European Patent Application No. 16150583.9 filed 8 Jan. 2016, European Patent Application No. 16150642.3 filed 8 Jan. 2016, European Patent Application No. 16150854.4 filed 12 Jan. 2016, European Patent Application No. 16151908.7 filed 19 Jan. 2016, European Patent Application No. 16156620.3 filed 22 Feb. 2016, and European Patent Application No. 16182376.0 filed 2 Aug. 2016 the entire disclosures of which are hereby incorporated by reference in their entireties.

The invention discloses a method for the preparation of thiophene-2-carbonyl chlorides starting from thiophenes with oxalyl chloride at elevated temperature with short reaction time.

BACKGROUND OF THE INVENTION

Thiophene-2-carbonyl chlorides are important synthetic intermediates, for instance for the synthesis of drugs and agrochemicals. They can be prepared by a number of different routes, each having advantages and disadvantages. Of particular interest are methods that only require inexpensive starting materials and reagents, are easy to perform, and generate only small amounts of waste.

Thiophene-2-carbonyl chloride is an intermediate for the preparation of Tioxazafen, a nematicide, with CAS 330459-31-9 and with the chemical name 3-phenyl-5-(thiophen-2-yl)-1,2,4-oxadiazole and which is the compound of formula (THIOXA-1).

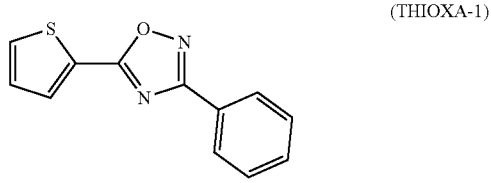 [SMILES: c1ccc(-c2noc(-c3cccs3)n2)cc1]

(THIOXA-1)

WO 2014/008257 A2 discloses the preparation of compound of formula (THIOXA-1).

5-Chloro-thiophene-2-carbonyl chloride is an intermediate for the preparation of Rivaroxaban, an anti-thrombotic agent, with CAS 366789-02-8 and with the chemical name (S)-5-Chlor-N-{2-oxo-3-[4-(3-oxomorpholin-4-yl)phenyl]-1,3-oxazolidin-5-ylmethyl}thiophen-2-carbamid and which is compound of formula (RIVA-1).

US 2003/0153610 A1 discloses Rivaroxaban and a method for its preparation, US 2015/0133657 A1 discloses another method for its preparation, U.S. Pat. No. 6,107,519 discloses certain precursors used in said preparation.

U.S. Pat. No. 4,321,399 discloses the preparation of thiophene-2-carbonyl chloride by a reaction of thiophene and phosgene in the presence of aluminum chloride and in a specific and inert organic solvent. In this method thiophene is added to a premixture of phosgene and aluminum chloride in the solvent. After the addition of thiophene the resulting mixture must be hydrolysed immediately by pouring the resulting mixture immediately into iced aqueous hydrochloric acid. The disclosure stresses the necessity of fast hydrolysis of the resulting mixture by advising a minimal continued contact of the thiophene with the premixture. Furthermore also higher concentration of thiophene are stated to have a negative effect on the yield, a content of only 5 to 10% of thiophene in the resulting mixture is advised. Therefore a continuous stream reaction is suggested in order to control these critical parameters, but such a continuous stream reaction is not disclosed. A draw back of a continuous reaction for the disclosed method is the insolubility of aluminum chloride in the solvent, because a suspension is formed which creates difficulties when conveyed by pumping through a continuous reactor set up due to clogging. Obviously when the disclosed reaction needs to be scaled up for production the disclosed "immediate hydrolysis" is no longer feasible, therefore the continuous reactor set up is actually mandatorily needed to ensure the required "immediate hydrolysis".

Edwards et al. in J. Org. Chem. 1966, 31, 1283 to 1285, disclose on page 1284 right column second paragraph, that thiophene is sensitive to acids and polymerizes to tar upon treatment with aluminum chloride: "With thiophene, aluminum chloride, and the same anhydride, tar formation was so great that the results were meaningless".

Also Geobaldo et al., Phys. Chem. Chem. Phys., 1999, 1, 561 to 569, warns on page 561 right column last paragraph, that thiophene is not stable under acidic conditions and is prone to electrophilic attack with the formation of stable oligomeric compounds.

Kuehnhanss et al., Journal für Praktische Chemie, 1956, 3, 137 to 145, reports specifically on page 144 a reaction of thiophene with oxalyl chloride at reflux temperature, which is below the boiling point of 61° C. for oxalyl chloride and of 84° C. for thiophene, followed by distillation and saponification, with a yield of 36.5% of thiophene-2-carboxylic acid. Reported on page 140 is an optimum of 60 h for the conversion, resulting in a yield of ca. 35%. Longer reaction times result in black condensation products, after 90 h no carbonyl chloride can be isolated anymore. The use of oxalyl chloride compared to the use of the carbamoyl chloride shows that oxalyl chloride has lower reactivity resulting in harder reaction conditions and lower yield (page 140), and therefore presents oxalyl chloride as a lesser attractive carboxylating agent than carbamoyl chloride. Carbamoyl chloride as carboxylating agent results in the formation of thiophene-2-carboxamide, which needs saponification with e.g. a base to provide the free acid, which again needs a conversion step to obtain the desired carbonyl chloride.

Comparative example 1 shows that even a molar excess of oxalyl choride of 5 times under the reaction conditions of Kuehnhanss did not improve the yield, but lowered the yield to ca. 9%.

There was a need for a method for preparation of thiophene-2-carbonyl chlorides that has few steps, with high yields, that does not need aluminum chloride or ammonium chloride, that does not create large amounts of salt as aluminum chloride for example would do, and that does not require mandatorily the use of a continuous reactor set up when it is scaled up for production.

Unexpectedly a method for preparation of thiophene-2-carbonyl chlorides starting from inexpensive thiophenes with oxalyl chloride was found which meets the needs mentioned above. Edwards, Geobaldo and Kuehnhanns stress the sensitivity of thiophenes against acid and its disposition to formation of oligomers and even tar at elevated temperature. Especially Kuehnhanns reports the formation of tar even at a low temperature resulting from the boiling point of oxalyl chloride. These comments discourage any treatment of thiophenes at elevated temperature above the boiling point of oxalyl chloride, especially not in the presence of acid. Contrary to this premonitions significantly higher yields compared to Kuehnhanns can be obtained at significantly higher temperatures than reported by Kuehnhanns. The purities are comparatively high, the reaction time is significantly shorter, no aluminum chloride is required, and the conversion of the thiophenes is complete. Despite the sensitivity of thiophenes towards acids, no significant amounts of byproducts are formed. Not steps such a saponification and conversion of a free acid to the acid chloride is required.

The following meanings are used,
halogen means F, Cl, Br or I, preferably Cl, Br or I, more preferably Cl or Br;
sulfolane CAS 126-33-0;
if not otherwise stated.

SUMMARY OF THE INVENTION

Subject of the invention is a method for the preparation of compound of formula (III);

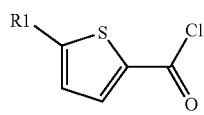
(III)

the method comprises a step ST1;
ST1 comprises a reaction REAC1 of compound of formula (II) with oxalyl chloride;
REAC1 is done at a temperature TEMP1 of 160 to 250° C. for a time TIME1 of from 10 sec to 24 h;

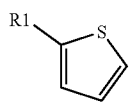
(II)

R1 is H or Cl.

DETAILED DESCRIPTION OF THE INVENTION

R1 is preferably H.
Preferably, the molar amount of oxalyl chloride is from 1.5 to 25 times, more preferably 1.5 to 20 times, even more preferably from 1.5 to 15 times, especially from 1.5 to 10 times, more especially from 1.5 to 7.5 times, even more especially from 1.5 to 6 times, based on the molar amount of compound of formula (II).

In another preferred embodiment, the molar amount of oxalyl chloride is from 1.75 to 25 times, more preferably 1.75 to 20 times, even more preferably from 1.75 to 15 times, especially from 1.75 to 10 times, more especially from 1.75 to 7.5 times, even more especially from 1.75 to 6 times, based on the molar amount of compound of formula (II).

Preferably, any excess of oxalyl chloride is recycled.
Preferably, TEMP1 is from 160 to 240° C., more preferably from 160 to 230° C., even more preferably from 160 to 220° C., especially from 160 to 210° C.
Preferably, the pressure PRESS1 of REAC1 is adjusted according to the vapor pressure of the reaction mixture at the chosen TEMP1 of REAC1; but PRESS1 can also be adjusted to a higher pressure than the vapor pressure at the chosen TEMP1. A PRESS1 higher than the vapor pressure of the reaction mixture at the chosen TEMP1 can be adjusted for example by applying inert gas such a nitrogen or argon to the reaction vessel.
Preferably, TIME1 is from 0.1 h to 24 h, more preferably from 0.1 h to 20 h, even more preferably from 0.1 h to 7.5 h, especially from 0.1 h to 6 h, more especially from 0.25 to 6 h, even more especially from 0.25 to 5.5 h.
In another preferred embodiment, TIME1 is from 10 sec to 20 h, more preferably from 10 sec to 7.5 h, even more preferably from 10 sec to 6 h, especially from 10 sec to 6 h, more especially from 10 sec to 5.5 h.
REAC1 can be done batch wise or continuously.
In case that REAC1 is done continuously, than preferably REAC1 is done in a device DEVICE1; DEVICE1 is preferably a tube, microreactor, shell and tube heat exchanger, plate heat exchanger and any common device which purpose is to exchange heat from or into a fluid;
more preferably in a tube.
The mixture REACMIX1 of compound of formula (II) with oxalyl chloride is heated in DEVICE1 to TEMP1.
Preferably REAC1 takes place in DEVICE1.
Preferably, TIME1 is the time, where REACMIX1 is exposed to heating to TEMP1, preferably in DEVICE1. During TIME1 REAC1 takes place. TIME1 is therefore preferably a residence time and is preferably the residence time of REACMIX1 in DEVICE1.
Preferably, REACMIX1 from DEVICE1 passes through a device DEVICE3, DEVICE3 is a device for back pressure regulation.
Preferably, DEVICE3 is a conventional back pressure regulating device.
PRESS1 in DEVICE1 is adjusted, controlled and maintained by the DEVICE3.
Conventional back pressure regulating devices, which can be used for DEVICE3, work either continuously or discontinually, i.e. by alternatingly opening and closing they release the product stream while holding the pressure. This leads naturally to variations in the pressure. In view of these possible variations of PRESS1 any pressure mentioned herein is meant to be an average pressure. Typical variations of the pressure are from +/−1 to +/−5 bar.
Preferably, PRESS1 is at least 20 bar, more preferably at least 30 bar, even more preferably at least 40 bar, especially at least 45 bar, more especially at least 50 bar, even more especially at least 55 bar, in particular at least 60 bar, more in particular at least 65 bar, even more in particular at least 70 bar, very even more in particular at least 75 bar, very, very even more in particular at least 80 bar.
The upper limit of the pressure is mainly determined by the devices and their ability to provide and/or stand the pressure. Purely out of such considerations and without limiting the invention, PRESS1 is preferably up to 500 bar, more preferably up to 400 bar, even more preferably up to 300 bar, especially up to 200 bar.
Preferably, PRESS1 is from 20 to 500 bar, more preferably from 30 to 500 bar, even more preferably from 40 to 500 bar, especially from 45 to 500 bar, more especially from 50 to 500 bar, even more especially from 55 to 500 bar, in particular from 60 to 500 bar, more in particular from 65 to 500 bar, even more in particular from 70 to 400 bar, very even more in particular from 75 to 300 bar, very, very even more in particular from 80 to 200 bar.

Preferably, the feeding of compound of formula (II) and of oxalyl chloride, either separately or in form of a mixture, is done by a device DEVICE0.

DEVICE0 is a pressuring device conventionally used to convey a fluid against pressure, such as a pump. When compound of formula (II) and oxalyl chloride are fed separately into DEVICE1, then preferably DEVICE0 has for each component reagent a respective device: a device DEVICE0-II for conveying the compound of formula (II), and a device DEVICE0-OXALYL for conveying the oxalyl chloride.

Preferably, DEVICE0 is the device that builds up PRESS1 in DEVICE1 against the DEVICE3.

Preferably, compound of formula (II) and oxalyl chloride are premixed and then are fed into DEVICE1.

REACMIX1 can pass through a device DEVICE2 after leaving DEVICE1 and before entering DEVICE3, DEVICE2 is a device for cooling REACMIX1.

Preferably, DEVICE2 is selected from the group consisting of tube, microreactor, shell and tube heat exchanger, plate heat exchanger and any common device which purpose is to exchange heat from a reaction mixture;
more preferably it is a tube.

Any heating, preferably in DEVICE1, can be done be any known means, preferably it is done by electric heating, microwave heating or by heating with a fluid heat carrier.

Any cooling, preferably in DEVICE2, can be done be any known means, preferably it is done by a fluid cooling medium.

Preferably, heating in DEVICE1 and any cooling in DEVICE2 is realized in form of a tube-in-tube set up, in form of a tube-in-container set up, in form of a shell and tube heat exchanger, plate heat exchanger or any common device which purpose is to exchange heat from a mixture or a reaction mixture;
more preferably, heating in DEVICE1 and any cooling in DEVICE2 is realized in form of a tube-in-tube set up or in form of a tube-in-container set up.

Preferably, DEVICE1 and any DEVICE2 are during operation in permanent fluid connection with each other and are both under PRESS1.

In case of DEVICE1 being a tube, then due to constructional limitations or due to density fluctuations and the like hot spots or cold spots can occur in spite of efforts to avoid them. Therefore any herein mentioned temperature is meant to be average temperature in view of possible hot or cold spots.

REACT can be done in the presence of sulfolane.

Preferably, the molar amount of sulfolane is from 2.5 to 25 times, more preferably from 5 to 25 times, even more preferably from 5 to 20 times, especially from 5 to 15 times, based on the molar amount of compound of formula (II).

After ST1, compound of formula (III) can be isolated and purified by methods well-known to those skilled in the art. These include, for instance, distillation, preferably fractional distillation, which can be done under reduced pressure, crystallization, extraction, or a combination of these methods.

Further subject of the invention is a method for the preparation of compound of formula (THIOXA);

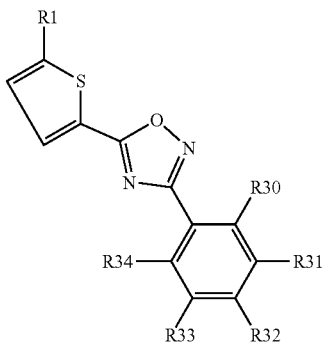

(THIOXA)

wherein the method comprises the step ST1;
R30, R31, R32, R33 and R34 are identical or different and independently from each other selected from the group consisting of H, halogen, $CF_3$, $CH_3$, $OCF_3$, $OCH_3$, CN and C(H)O;
wherein ST1 and R1 are as defined herein, also with all their embodiments;
especially wherein R1 is H;
in another especial embodiment R30, R31, R32, R33 and R34 are H;
more especially wherein R1, R30, R31, R32, R33 and R34 are H.

Preferably, the method for preparation of compound of formula (THIOXA) starting from compound of formula (III) has a step ST3;
ST3 is done after ST1;
ST3 comprises a reaction REAC3, in REAC3 the compound of formula (III) is reacted with a compound of formula (IV).

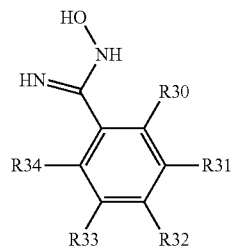

(IV)

Details for ST3 are disclosed in WO 2014/008257 A2.
Specific embodiments for ST3 are disclosed in the examples 2, 3, 7, 9 and 12 of WO 2014/008257 A2
Preferably, compound of formula (IV) is selected from the group consisting of compound of formula (IV-1), compound of formula (IV-2), compound of formula (IV-3), compound of formula (IV-4), compound of formula (IV-5), compound of formula (IV-6) and compound of formula (IV-7);

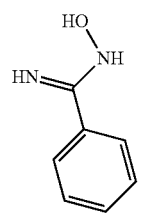

(IV-1)

(IV-2)
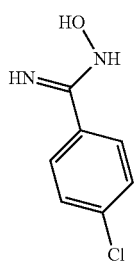

(IV-3)
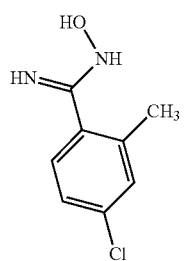

(IV-4)
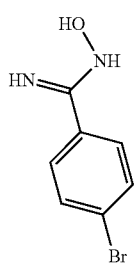

(IV-5)
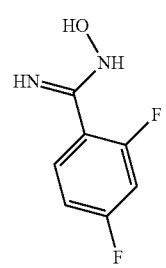

(IV-6)
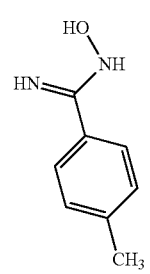

(IV-7)
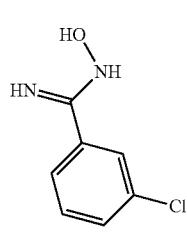

more preferably, compound of formula (IV) is compound of formula (IV-1) or compound of formula (IV-2).

When compound of formula (III) is brought into contact with compound of formula (IV) a reaction mixture is formed.

Preferably, REAC3 is done in the presence of a solvent SOLV3.

Preferably, SOLV3 is a water-immiscible organic solvent.

Preferably, SOLV3 solubilizes compound of formula (IV) and compound of formula (THIOXA).

Preferably, SOLV3 forms an azeotrope with water.

Preferably, SOLV3 is selected from the group consisting of 2-methyltetrahydrofuran and butyl acetate;

more preferably, SOLV3 is 2-methyltetrahydrofuran.

Preferably, REAC3 is done in the presence of a base BAS3.

Preferably, BAS3 is an aqueous base.

Preferably, BAS3 is selected from the group consisting of sodium hydroxide, potassium hydroxide, lithium hydroxide, and calcium hydroxide.

Preferably, the reaction mixture of REAC3 comprises an organic phase and an aqueous phase.

Preferably, the pH of the aqueous phase is greater than 8, more preferably greater than 10.

Preferably, the pH of the aqueous phase is increased or maintained by adding additional BAS3 to the reaction mixture or REAC3.

Preferably, the temperature of REAC3 is no greater than 85° C.;

more preferably, the temperature of REAC3 is maintained at from 55° C. to 75° C.

Preferably, REAC3 is done in the presence of a phase transfer catalyst PTC3.

Preferably, PTC3 is selected from the group consisting of quaternary ammonium salts, phosphonium salts, and crown ethers;

more preferably, PTC3 is selected from the group consisting of tetrabutylammonium hydroxide, tetrabutylammonium bromide, tetrabutylammonium fluoride, tetrabutylammonium iodide, tetrabutylphosphonium bromide, tetrabutylphosphonium chloride, and benzyltrimethylammonium hydroxide;

even more preferably, PTC3 is tetrabutylammonium hydroxide.

Preferably, compound of formula (IV) is dissolved in SOLV3 prior to adding the compound of formula (III) to form the reaction mixture of REAC3.

Preferably, REAC3 is done in the presence of water.

Further subject of the invention is a method for the preparation of compound of formula (RIVA-I);

(RIVA-I)
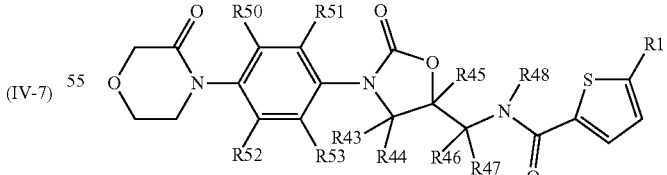

R50, R51, R52 and R53 are identical or different and independently of one another each is selected from the group consisting of H, halogen, $CF_3$, CN, $NO_2$, C(O)—$NH_2$, C(O)—$C_{1-6}$ alkyl, O—R60; N(R60)R61 and $C_{1-6}$ alkyl;

R60 and R61 are identical or different and independently of one another each is selected from the group consisting of H, $C_{1-4}$ alkyl and C(O)R63;

R63 is selected from the group consisting of $C_{1-4}$ alkyl-$NH_2$, $NH_2$, $NH$—$C_{1-4}$ alkyl, $N(C_{1-4}$ alkyl$)C_{1-4}$ alkyl and $C_{1-8}$ alkyl;

R43, R44, R45, R46, R47 and R48 are identical or different and independently of one another each represents H or $C_{1-6}$ alkyl;

wherein the method comprises the step ST1;

wherein ST1 and R1 are as defined herein, also with all their embodiments;

preferably, R1 is Cl;

especially wherein the compound of formula (RIVA-I) is the compound of formula (RIVA-II);

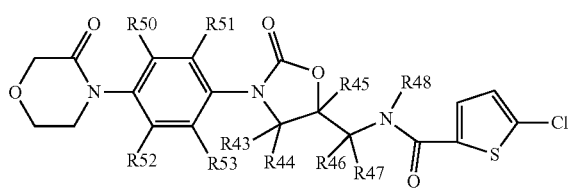

(RIVA-II)

wherein R50, R51, R52, R53, R43, R44, R45, R46, R47 and R48 are as defined herein, also with all their embodiments;

more especially wherein the compound of formula (RIVA-I) is the compound of formula (RIVA-1).

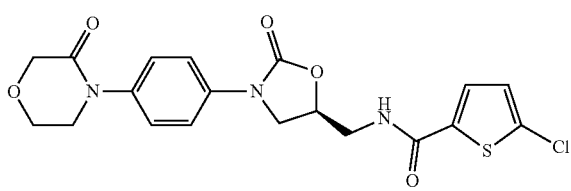

(RIVA-1)

Preferably, the method for preparation of compound of formula (RIVA-I) starting from compound of formula (III) has a step ST4;

ST4 is done after ST1;

ST4 comprises a reaction REAC4, in REAC4 the compound of formula (III) is reacted with a compound of formula (RIVA-Ia);

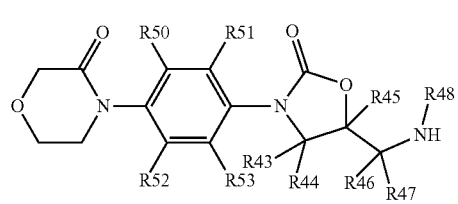

(RIVA-Ia)

preferably, R1 is Cl;

more preferably, R1 is Cl and compound of formula (RIVA-Ia) is compound of formula (RIVA-1a).

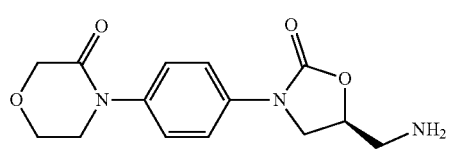

(RIVA-1a)

Details for ST4 are disclosed in US 2003/0153610 A1.

Preferably, REAC4 is done in a solvent SOLV4, SOLV4 is selected from the group consisting of halogenated hydrocarbons, ethers, alcohols, hydrocarbons, dimethylformamide, dimethyl sulphoxide, acetonitrile, pyridine, hexamethylphosphoric triamide, water and mixtures thereof.

Halogenated hydrocarbons are preferably selected from the group consisting of dichloromethane, trichloromethane, carbon tetrachloride, 1,2-dichloroethane, trichloroethane, tetrachloroethane, 1,2-dichloroethylene and trichloroethylene.

Ethers are preferably selected from the group consisting of diethyl ether, methyl tert-butyl ether, dioxane, tetrahydrofuran, glycol dimethyl ether and diethylene glycol dimethyl ether.

Alcohols are preferably selected from the group consisting of methanol, ethanol, propanol, butanol.

Hydrocarbons are preferably selected from the group consisting of benzene, xylene, toluene, hexane and cyclohexane.

REAC4 can be done in the presence of a base BAS4, BAS4 can be any customary inorganic or organic base.

BAS4 is preferably selected from the group consisting of alkali metal hydroxide, alkali metal carbonate, sodium methoxide, potassium methoxide, sodium ethoxide, potassium ethoxide, potassium-tert-butoxide, amide, amine, and mixtures thereof;

alkali metal hydroxide is preferably sodium hydroxide or potassium hydroxide;

alkali metal carbonate is preferably sodium carbonate or potassium carbonate;

amide is preferably selected from the group consisting of sodium amide, lithium bis-(trimethylsilyl)amide and lithium diisopropylamide;

amine is preferably selected from the group consisting of triethylamine, diisopropylethylamine, diisopropylamine, 4-N,N-dimethylaminopyridine and pyridine.

BAS4 can be employed in an amount of from 1 to 5 mol, preferably from 1 to 2 mol, based on 1 mol of compound of formula (RIVA-Ia).

Preferably, REAC4 is done at a reaction temperature of from −78° C. to reflux temperature, more preferably from 0° C. to reflux temperature, with the reflux temperature being the reflux temperature under the respective pressure.

Preferably, REAC4 is done at a pressure of from 0.5 to 5 bar, more preferably at atmospheric pressure.

In case that compound of formula (RIVA-I) is compound of formula (RIVA-1) and R1 is Cl, then in another preferred embodiment the preparation of compound of formula (RIVA-1) starting from compound of formula (III) with R1 being Cl has a step ST5;

details for ST5 are disclosed in US 2015/0133657 A1;

ST5 is done after ST1;

ST5 comprises a reaction REAC5, in REAC5 compound of formula (III) with R1 being Cl is reacted with a compound of formula (RIVA-10);

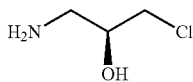
(RIVA-10)

the reaction product of REAC5 is compound of formula (RIVA-11);

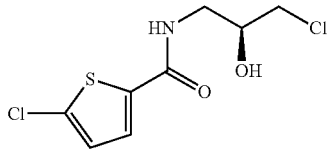
(RIVA-11)

preferably, after ST5 a step ST6 is done;

ST6 comprises a reaction REAC6, in REAC6 compound of formula (RIVA-11) is reacted with a compound of formula (RIVA-12) in the presence of phosgene or a phosgene equivalent;

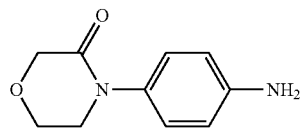
(RIVA-12)

the reaction product of REAC6 is compound of formula (RIVA-13);

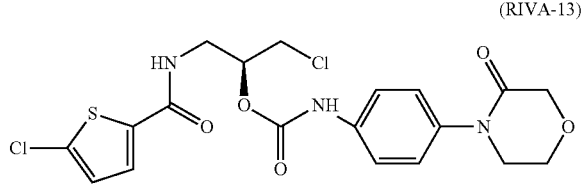 [SMILES: O=C(Nc1ccc(N2CCOCC2=O)cc1)O[C@H](CCl)CNC(=O)c1ccc(Cl)s1]
(RIVA-13)

preferably, after ST6 a step ST7 is done;

ST7 comprises a reaction REAC7, in REAC7 compound of formula (RIVA-13) is cyclized to obtain compound of formula (RIVA-1).

The phosgene equivalent is preferably diphosgene or triphosgene or a carbon monoxide equivalent.

A carbon monoxide equivalent is preferably carbonyldiimidazole or disuccinimidyl carbonate.

Compound of formula (RIVA-10) can also be used in form of a salt thereof, preferably as a hydrochloride salt. Compound of formula (RIVA-10) is a known compound and can be prepared according to known method, e.g. as disclosed in U.S. Pat. No. 6,107,519 or in US 2015/0133657 A1.

Preferably, REAC5 is done in the presence of a base, such as sodium bicarbonate.

Preferably, REAC5 is done in a solvent, the solvent can be ethyl acetate, hexane, water, toluene or a mixture thereof.

Preferably, the reaction temperature of REAC5 is from 0 to 40° C.

Preferably, the reaction time of REAC5 is from 0.5 to 10 h.

The compound of formula (RIVA-11) may be isolated from the reaction mixture after REAC5 by methods including layer separation, concentration, distillation, decantation, filtration, evaporation, centrifugation, or a combination thereof, and may further be dried.

Preferably, REAC6 is done in a solvent. The solvent in REAC6 can be dichloromethane, dichloroethane, or a mixture thereof.

REAC6 can be done in the presence of a base, The base in REAC6 can be pyridine, dimethylaminopyridine, triethylamine, sodium carbonate, potassium carbonate, or a mixture thereof; more preferably pyridine, triethylamine, sodium carbonate, potassium carbonate, or a mixture thereof.

Preferably, the reaction time of REAC6 is from 0.5 to 10 h.

Preferably, the reaction temperature of REAC6 is from 0 to 35° C.

Preferably, in a first step of REAC6 the phosgen or phosgene equivalent is mixed with compound of formula (RIVA-11), optionally also with the base of REAC6, optionally in the solvent of REAC6, thereafter in a second step of REAC6 compound of formula (RIVA-12) is added.

Preferably, the reaction time of the first step of REAC6 is from 0.5 to 4 h.

Preferably, the reaction temperature of the first step of REAC6 is from 5 to 25° C.

Preferably, the reaction time of the second step of REAC6 is from 0.5 to 6 h.

Preferably, the reaction temperature of the second step of REAC6 is from 10 to 35° C.

The compound of formula (RIVA-13) may be isolated from the reaction mixture after REAC6 by methods including layer separation, concentration, distillation, decantation, filtration, evaporation, centrifugation, or a combination thereof, and may further be dried.

Preferably, the cyclization of REAC7 is done in a solvent. The solvent in REAC7 can be acetone, acetonitrile, methanol, ethanol, isopropanol, dioxane, tetrahydrofuran, water, or a mixture thereof.

REAC7 can be done in the presence of a base. The base in REAC7 can be potassium carbonate, potassium bicarbonate, potassium hydroxide, sodium hydroxide, sodium carbonate, sodium bicarbonate, sodium hydride, or a mixture thereof.

The base in REAC7 may be added to the mixture containing the compound of formula (RIVA-13) and the solvent of REAC7 or a mixture containing the compound of formula (RIVA-13) in which it is formed in REAC6.

Preferably, the reaction temperature of REAC7 is of from 10 to 40° C.

Preferably, the reaction time of REAC7 is from 2 to 15 h.

Compound of formula (RIVA-I), compound of formula (RIVA-II) and compound of formula (RIVA-1) may be isolated from any reaction mixture by methods including layer separation, concentration, distillation, decantation, filtration, evaporation, centrifugation, or a combination thereof, and may further be dried.

EXAMPLES

Internal standard for $^1$H NMR: Triisobutyl phosphate, if not otherwise stated

Example 1: thiophene-2-carbonyl chloride

A mixture of thiophene (11.2 ml, 0.14 mol) and oxalyl chloride (47.6 ml, 0.56 mol) was stirred in an autoclave at 200° C. for 2 h, whereby the pressure increased to 40 bar. Distillation of the resulting mixture under reduced pressure yielded 11.8 g (58% yield) of thiophene-2-carbonyl chloride.

$^1$H NMR (CDCl$_3$, 400 MHz) delta=7.99 (d, br, J=4 Hz, 1H), 7.83 (d, br, J=4 Hz, 1H), 7.20 (t, J=4 Hz, 1H).

Examples 2 to 9: thiophene-2-carbonyl chloride

A sample of a mixture of oxalyl chloride and thiophene (2:1, molar ratio) was heated in a closed vessel to 200° C. for 2 h. Analysis of the reaction mixture by $^1$H NMR with an internal standard indicated a conversion of thiophene of 100% and a yield of thiophene-2-carbonyl chloride of 72%.

3 mmol thiophene were used in examples 2 to 5, 0.1 mmol thiophene were used in examples 6 to 9.

| Example | m.r.$^{(1)}$ | T [° C.] | t | conv$^{(2)}$ | yield$^{(3)}$ |
|---|---|---|---|---|---|
| 3 | 5 | 200 | 2.0 h | 100% | 68% |
| 4 | 5 | 200 | 5.0 h | 100% | 60% |
| 5 | 2 | 200 | 1.0 h | 99% | 62% |
| 6 | 2$^{(4)}$ | 180 | 1.5 h | 100% | 83% |
| 7 | 2$^{(4)}$ | 180 | 0.5 h | 81% | 57% |
| 8 | 2$^{(4)}$ | 170 | 1.5 h | 98% | 83% |
| 9 | 2$^{(4)}$ | 170 | 3.0 h | 100% | 82% |

$^{(1)}$m.r.: molar ratio of oxalyl chloride to thiophene
$^{(2)}$conv: conversion of thiophene
$^{(3)}$yield of thiophene-2-carbonyl chloride
$^{(4)}$sulfolane (10 mol % of amount of thiophene) was added to the mixture of oxalyl chloride and thiophene before the heating in the closed vessel Example 10: 5-chloro-2-thiophenecarbonyl chloride A mixture of oxalyl chloride, 2-chlorothiophene and sulfolane (3:1:0.33, molar ratio) was heated in a closed vessel to 180° C. for 1 h 40 min. Analysis of the reaction mixture by $^1$H NMR indicated a conversion of 2-chlorothiophene of 85% and a yield of 5-chlorothiophene-2-carbonyl chloride of 71%.

$^1$H NMR (CDCl$_3$, 400 MHz) delta=7.79 (d, J=4 Hz, 1H), 7.04 (d, J=4 Hz, 1H).

$^{13}$C NMR (CDCl$_3$, 100 MHz) delta=158.8, 143.3, 137.6, 135.2, 128.3.

Example 11: 5-chloro-2-thiophenecarbonyl chloride

A mixture of oxalyl chloride, 2-chlorothiophene and sulfolane (3:1:0.33, molar ratio) was heated in a closed vessel to 165° C. for 17.5 h. Analysis of the reaction mixture by $^1$H NMR indicated a conversion of 2-chlorothiophene of 100% and a yield of 5-chlorothiophene-2-carbonyl chloride of 100%.

Comparative Example 1: According to Kuehnhanss et al., Journal für Praktische Chemie, 1956, 3, Page 144, Using 5 Equivalents of oxalyl chloride Instead of 1 Equivalent A mixture of oxalyl chloride and thiophene in the molar ratio of 5:1 was stirred under reflux for 60 h. Distillation of the reaction mixture yielded 2-thiophenecarbonyl chloride in ca. 9% yield.

Example 12: thiophene-2-carbonyl chloride in a Tubular Reactor

DEVICE0: piston pump 260D from ISCO Teledyne
DEVICE1: tubular reactor with a length of 6 m, with an internal volume of 96.16 mL and an outer diameter of 0.25 inch
DEVICE3: pressure control valve Swagelok BPV-SS-07

A mixture of oxalyl chloride and thiophene with a molar ratio of 2:1 was fed by DEVICE0 with a rate of 1.01 mL/min through DEVICE1 at an average PRESS1 of 80 bar which was adjusted and held by the means of DEVICE3. DEVICE1 was maintained at a temperature of 200° C. by means of a heating fluid. The residence time TIME1 of the mixture in DEVICE1 was 95.7 min. A liquid sample of 325.5 g of the reaction mixture was collected during 6.5 h. Analysis of the reaction mixture by $^1$H NMR with the internal standard dioxane showed a conversion of thiophene of 100% and a yield of thiophene-2-carbonyl chloride of 90.5% based on thiophene.

Example 13: thiophene-2-carbonyl chloride in a Tubular Reactor

DEVICE0: piston pump 260D from ISCO Teledyne
DEVICE1: tubular reactor with a length of 6 m, with an internal volume of 5.86 mL and an outer diameter of 0.0625 inch
DEVICE3: pressure control valve Swagelok BPV-SS-07

A mixture of oxalyl chloride and thiophene with a molar ratio of 2:1 was fed by DEVICE0 with a rate of 0.05 mL/min through DEVICE1 at an average PRESS1 of 80 bar which was adjusted and held by the means of DEVICE3. DEVICE1 was maintained at a temperature of 180° C. by means of a heating fluid. The residence time TIME1 of the mixture in DEVICE1 was 120 min. A liquid sample of the reaction mixture was collected and analyzed by $^1$H NMR with the internal standard dioxane, yield of thiophene-2-carbonyl chloride was 79.3% based on thiophene.

Example 14: thiophene-2-carbonyl chloride in a Tubular Reactor

DEVICE0: piston pump 260D from ISCO Teledyne
DEVICE1: tubular reactor with a length of 6 m, with an internal volume of 96.16 mL and an outer diameter of 0.25 inch
DEVICE3: pressure control valve Swagelok BPV-SS-07

A mixture MIX1 containing 90 wt % of a mixture MIX2 of oxalyl chloride and thiophene with a molar ratio of 2:1, and 10 wt % sulfolane, the wt % being based on the total weight of the MIX1, was fed by DEVICE0 with a rate of 2.14 mL/min through DEVICE1 at an average PRESS1 of 80 bar which was adjusted and held by the means of DEVICE3. DEVICE1 was maintained at a temperature of 200° C. by means of a heating fluid. The residence time TIME1 of the mixture in DEVICE1 was 45 min. A liquid sample of the reaction mixture was collected and analyzed by $^1$H NMR with the internal standard dioxane, yield of thiophene-2-carbonyl chloride was 93% based on thiophene.

Example 15: thiophene-2-carbonyl chloride in a Tubular Reactor

DEVICE0: piston pump 260D from ISCO Teledyne
DEVICE1: tubular reactor with a length of 6 m, with an internal volume of 96.16 mL and an outer diameter of 0.25 inch
DEVICE3: pressure control valve Swagelok BPV-SS-07

A mixture of oxalyl chloride and thiophene with a molar ratio of 2:1 was fed by DEVICE0 with a rate of 1.592 mL/min through DEVICE1 at an average PRESS1 of 80 bar which was adjusted and held by the means of DEVICE3. DEVICE1 was maintained at a temperature of 227° C. by means of a heating fluid. The residence time TIMET of the mixture in DEVICE1 was 60.4 min. A liquid sample of the reaction mixture was collected and analyzed by $^1$H NMR with the internal standard dioxane, yield of thiophene-2-carbonyl chloride was 85.3% based on thiophene.

The invention claimed is:

1. A method for the preparation of compound of formula (III);

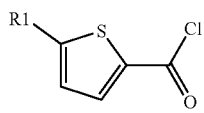

wherein the method comprises a step ST1;

ST1 comprises a reaction REAC1 of compound of formula (II) with oxalyl chloride;

REAC1 is done at a temperature TEMP1 of 160 to 250° C. for a time TIME1 of from 10 seconds to 24 hours; and wherein the molar amount of oxalyl chloride is from 1.5 to 25 times based on the molar amount of compound of formula (II);

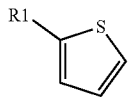

wherein R1 is H or Cl.

2. The method according to claim 1, wherein R1 is H.

3. The method according to claim 1, wherein the molar amount of oxalyl chloride is from 1.75 to 25 times based on the molar amount of compound of formula (II).

4. The method according to claim 1, wherein TEMP1 is from 160 to 240° C.

5. The method according to claim 1, wherein TIME1 is from 10 seconds to 20 hours.

6. The method according to claim 1, wherein REAC1 is be done in the presence of sulfolane.

7. The method according to claim 6, wherein the molar amount of sulfolane is from 2.5 to 25 times based on the molar amount of compound of formula (II).

8. The method according to claim 1, wherein REAC1 is done continuously.

9. A method for the preparation of compound of formula (THIOXA);

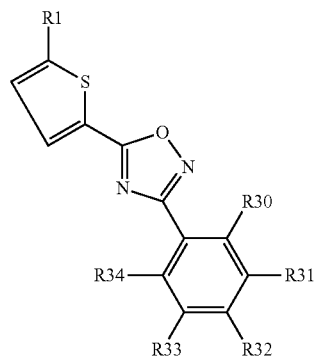

wherein the method comprises the step ST1 and a step ST3;

wherein ST1 is as defined in claim 1 and R1 is defined in claim 1;

wherein ST3 comprises a reaction REAC3 of the compound of formula (III) prepared from ST1 with a compound of formula (IV)

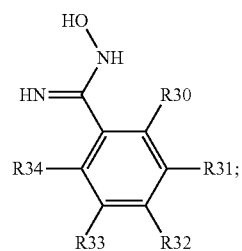

and wherein R30, R31, R32, R33 and R34 are identical or different and independently from each other selected from the group consisting of H, halogen, $CF_3$, $CH_3$, $OCF_3$, $OCH_3$, CN and C(H)O.

10. The method according to claim 9, wherein R30, R31, R32, R33 and R34 are H.

11. The method according to claim 10, wherein R1 is H.

12. A method for the preparation of compound of formula (RIVA-I);

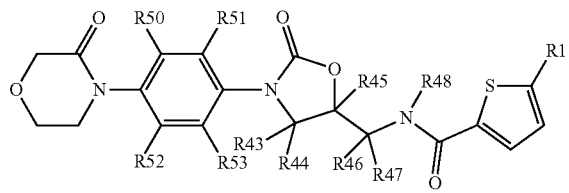

wherein R50, R51, R52 and R53 are identical or different and independently of one another each is selected from the group consisting of H, halogen, $CF_3$, CN, $N_{O2}$, $C(O)$—$NH_2$, $C(O)$—$C_{1-6}$ alkyl, O—R60; N(R60)R61 and $C_{1-6}$ alkyl;

wherein R60 and R61 are identical or different and independently of one another each is selected from the group consisting of H, $C_{1-4}$ alkyl and C(O)R63;

wherein R63 is selected from the group consisting of $C_{1-4}$ alkyl-$NH_2$, $NH_2$, NH—$C_{1-4}$ alkyl, N($C_{1-4}$ alkyl)$C_{1-4}$ alkyl and $C_{1-8}$ alkyl;

wherein R43, R44, R45, R46, R47 and R48 are identical or different and independently of one another each represents H or $C_{1-6}$ alkyl;

wherein the method comprises the step ST1 and a step ST4;

wherein ST1 is as defined in claim 1;

R1 is as defined in claim 1; and

ST4 comprises a reaction REAC4 of the compound of formula (III) prepared by ST1 with a compound of formula (RIVA-Ia)

(RIVA-Ia)

13. The method according to claim 12, wherein R1 is H.

14. The method according to claim 12, wherein the compound of formula (RIVA-I) is the compound of formula (RIVA-1).

* * * * *